United States Patent

Kelley et al.

[11] Patent Number: 5,480,484
[45] Date of Patent: Jan. 2, 1996

[54] CYTOLOGY CENTRIFUGE APPARATUS

[75] Inventors: Thomas F. Kelley, Canton, Mass.; Alton D. Floyd, Edwardsburg, MD.

[73] Assignee: StatSpin Technologies, Norwood, Mass.

[21] Appl. No.: 204,608

[22] Filed: Mar. 1, 1994

[51] Int. Cl.⁶ .................................................. B05C 13/00
[52] U.S. Cl. .................... 118/52; 206/456; 210/380.1; 422/72; 422/101; 422/104; 436/45; 436/46; 494/16; 494/20
[58] Field of Search ............... 118/52, 416; 427/240; 494/16, 20; 210/380.1; 422/72, 101, 104; 436/45, 46; 435/312; 206/456

[56] References Cited

U.S. PATENT DOCUMENTS

| | | | |
|---|---|---|---|
| 3,577,267 | 5/1971 | Preston, Jr. et al. | 117/101 |
| 3,705,048 | 12/1972 | Staunton | 117/3 |
| 3,870,014 | 3/1975 | Buck | 118/52 |
| 4,016,828 | 4/1977 | Maher, Jr. et al. | 118/6 |
| 4,031,852 | 6/1977 | Clarke et al. | 118/52 |
| 4,037,003 | 7/1977 | Maher, Jr. et al. | 427/2 |
| 4,103,643 | 8/1978 | Staunton | 118/50 |
| 4,108,109 | 8/1978 | Barger et al. | 118/52 |
| 4,197,329 | 4/1980 | Holroyd et al. | 427/2 |
| 4,209,548 | 6/1980 | Bacus | 427/2 |
| 4,266,505 | 5/1981 | Bacus | 118/699 |
| 4,280,442 | 7/1981 | Johnson | 118/52 |
| 4,294,866 | 10/1981 | Johnson | 427/2 |
| 4,349,275 | 9/1982 | Ayotte et al. | 356/36 |
| 4,391,710 | 7/1983 | Gordon | 210/361 |
| 4,468,410 | 8/1984 | Zeya | 427/2 |
| 4,576,110 | 3/1986 | Wells | 118/52 |
| 4,633,804 | 1/1987 | Arii | 118/52 |
| 4,819,804 | 4/1989 | Levy | 206/456 |
| 4,853,188 | 8/1989 | Toya | 422/72 |
| 4,941,426 | 7/1990 | Sago et al. | 118/52 |
| 5,009,185 | 4/1991 | Stokes et al. | 118/52 |
| 5,252,228 | 10/1993 | Stokes et al. | 210/781 |
| 5,292,000 | 3/1994 | Levy | 206/456 |
| 5,326,398 | 7/1994 | Kelley et al. | 118/52 |

OTHER PUBLICATIONS

Product Literature entitled "Introducing CYTOPRO Cytocentrifuge Making a Tough Job Easier", dated 1992, of Wescor, Inc., 459 South Main Street, Logan, Utah 84321, consisting of six unnumbered pages.

Product Literature entitled "2. Operating the Cytospin 3", from Shandon Operator's Manual, dated 1987, of Shandon Inc., 171 Industry Drive, Pittsburgh, Pa. 15275, consisting of four pages in non–sequential order.

Primary Examiner—David L. Lacey
Assistant Examiner—Laura E. Edwards
Attorney, Agent, or Firm—Weingarten, Schurgin, Gagnebin & Hayes

[57] ABSTRACT

Improved cytology centrifuge apparatus includes single or multiple well cell concentrators for being rotated by a centrifugal spinner. A rotor is removably supported by the spinner for rotation and is adapted to receive two or four cell concentrators. The rotor supports the cell concentrators in an unrestrained manner, thereby enhancing the ease of use and flexibility of the apparatus. Each cell concentrator includes a chamber having a top surface in which at least one fluid receiving aperture is disposed and a front surface in which at least one fluid expulsion aperture is disposed. A backing plate is provided with protruding top and bottom edges to vertically align a microscope slide with the chamber so that the fluid expulsion aperture is adjacent to a central portion of the slide. Retention clips secure the chamber to the backing plate with the slide sandwiched therebetween in horizontal alignment. The cell concentrator is shaped to rest stably on a planar surface in a tilted manner so that a fluid specimen contained therein is prevented from contacting the slide prior to centrifugation. The concentrator is also well suited for use as a staining chamber and the backing plate has a viewing aperture aligned with the fluid expulsion aperture to enable viewing of cells on the slide during a staining process.

29 Claims, 6 Drawing Sheets

CYTOLOGY CENTRIFUGE APPARATUS

FIELD OF THE INVENTION

This invention relates generally to centrifuge apparatus and more particularly, to improved cytology centrifuge apparatus.

BACKGROUND OF THE INVENTION

Centrifugation of cells suspended in a carrier fluid in order to deposit the cells on a microscope slide for subsequent analysis is known in the field of cytology. Exemplary cell suspension fluids include normal body fluids such as synovial fluid or cerebrospinal fluid, abnormal fluids such as ascites fluid resulting from a cancer, or artificial fluids such as cell cultures. During centrifugation, the carrier fluid is forced against the slide causing cells suspended therein to attach to the slide, preferably in a substantially monolayer configuration. Subsequent processing may include staining the deposited cells with staining reagents to enhance selected cell attributes prior to microscopic analysis of the cells.

Generally, centrifugation apparatus includes an electromechanical spinner for supporting a rotor and having a motor for rotating the rotor. The rotor includes a mechanism for mounting and restraining one or more sample chambers, referred to hereinafter as cell concentrators, for rotation. The cell concentrators include generally, a chamber having a fluid receiving aperture through which a fluid specimen is added and a fluid expulsion aperture through which the fluid is expelled during centrifugation, a microscope slide disposed in fluid communication with the fluid expulsion aperture, and a securing mechanism for securing the slide to the chamber.

Since some of the materials to be centrifuged may be toxic or present a biohazard, various schemes are employed to promote the safer use of centrifuges. One technique for improving the safety of the centrifugation process is to provide a removable rotor so that the cell concentrators can be mounted in the rotor, loaded with specimens and, after centrifugation, removed from the rotor in a safe environment such as in some type of biological safety cabinet.

Bibulous paper, sometimes referred to as a filter card, is often disposed between the chamber and the microscope slide and comprises a fibrous material for absorbing carrier fluid. More particularly, the bibulous paper has an aperture aligned with the fluid expulsion aperture in the chamber so that, theoretically, fluid communication between the chamber and the slide is not impaired. However, due to the location of the bibulous paper relative to the slide, the paper may absorb the carrier fluid so rapidly that cells are absorbed and lost to analysis. Moreover, the capacity and rate of absorption of carrier fluid by the bibulous paper are difficult to control and depend on such variables as the force applied by the securing mechanism which secures the chamber to the slide, the uniformity of such force, the amount of carrier fluid, and the duration of centrifugation. Another potential drawback to the use of bibulous paper interposed between the chamber and the slide is possible contamination of the deposited cells by fibers of the paper itself. Significantly, bibulous paper has a limited fluid retention capacity. Once saturated, excess fluid in the carrier is spun off and flung at a relatively high velocity against the outside of the rotor creating potentially dangerous aerosols.

As is believed in the field of cytology centrifugation, it is desirable to keep the carrier fluid from contacting the microscope slide prior to centrifugation. Theoretically, this practice enhances the uniformity of the cell deposition and is essential where bibulous paper is inserted between the chamber and the slide since fluid contact with the bibulous paper will result in undesirable cell absorption.

SUMMARY OF THE INVENTION

In accordance with the invention, cytology centrifuge apparatus is provided with an improved single or multiple well cell concentrator. The concentrator includes a chamber having a top surface in which at least one fluid receiving aperture is disposed and a front surface in which at least one fluid expulsion aperture is disposed. Each fluid receiving aperture and fluid expulsion aperture pair defines a well of the chamber and, in the multiple well concentrator, adjacent wells are isolated by separating walls. In operation, a fluid specimen, such as a carrier fluid with cells suspended therein, is inserted into the fluid receiving aperture of each well. The associated fluid expulsion aperture permits expulsion of the fluid onto an adjacently held microscope slide during centrifugation for deposition of the cells. A backing plate having protruding top and bottom edges is secured, or clamped to the chamber by a pair of clips with the slide sandwiched therebetween. The top and bottom edges of the backing plate maintain the chamber and slide in vertical alignment and the clips maintain the chamber and slide in horizontal alignment.

An electromechanical spinner is provided with a central depression, or bowl, for removably supporting a rotor for rotation. The rotor has multiple positions for receiving two or four cell concentrators in an unrestrained manner, thereby enhancing the ease of use of the apparatus. With this arrangement, the need for a mechanism for mounting and restraining the concentrators in the rotor is eliminated since the concentrators rest freely in a corresponding rotor position prior to, during, and after centrifugation.

Each cell concentrator is shaped to rest stably on a planar surface in a tilted manner. More particularly, the bottom edge of the backing plate has a beveled portion which causes the cell concentrator to rest stably in a tilted position until the concentrator is subjected to centrifugal forces during centrifugation. When a concentrator is placed unrestrained in the rotor in its tilted position prior to centrifugation, specimen fluid therein is kept away from the fluid expulsion aperture and the adjacent slide, thereby enhancing the uniformity of cell deposition on the slide.

During centrifugation, rotation of the rotor and concomitant rotation of the concentrators contained therein, causes the concentrators to pivot to a vertical orientation, with the backing plate contacting an adjacent inner sidewall of the rotor. After centrifugation, the cell concentrators automatically pivot back to their tilted positions in which carrier fluid flows away from the slide.

The rotor has a ledge around the upper perimeter thereof and a cover is provided for resting on the ledge to cover the rotor. Even if the wells of the cell concentrators are overfilled with a fluid specimen, the excess fluid will leave the chamber as soon as the concentrator begins to pivot to the vertical position and while the rotor is rotating at a relatively slow speed. Such fluid will flow to the adjacent inner sidewall of the rotor and be trapped under the ledge. With this arrangement, the formation of potentially harmful aerosols, such as, may occur when fluid is flung at a high speed onto a distant surface is prevented.

The tilted position which the concentrators resume after centrifugation facilitates removal of carrier fluid by aspiration with a pipette inserted into the one or more wells through the corresponding fluid receiving aperture. The cell concentrator can be disassembled and the slide then processed by any of various fixing and staining procedures. Or, when the cell concentration of the sample fluid was very low, additional aliquots of the specimen can be added and reprocessed, or respun to increase the number of cells on the slide.

Cell staining can be achieved in the assembled concentrator. That is, once centrifugation is completed (and carrier fluid removed), staining reagents may be introduced into the one or more wells by a pipette inserted through the corresponding fluid receiving aperture. More particularly, the concentrator is first inverted so that the slide is resting in a horizontal orientation. Stain flows through the fluid expulsion aperture to contact cells attached to the slide. Use of the concentrator as a staining chamber is possible since there is no bibulous paper between the chamber and the slide which would absorb the stain. The relatively small well volume, shallow wells, and preferred fabrication of the chamber from a transparent material further facilitate use of the concentrator for staining deposited cells. The ability to stain cells in the assembled concentrator is desirable since controlled and repeatable application of staining reagents is possible, thereby minimizing waste of expensive staining reagents. Staining reagent waste is further reduced since reagent evaporation is minimized in the substantially closed concentrator.

A viewing aperture is provided in the backing plate adjacent to the at least one fluid expulsion aperture in order to permit viewing of sedimented and attached cells during the staining process from the rear surface of the slide. More particularly, the cells can be viewed during the staining process by inverting the concentrator and placing it under a conventional microscope. Alternatively, an inverted microscope may be used to eliminate the need for inverting the cell concentrator. Viewing cells during the staining process may be desirable for use in developing optimum staining processes.

In one embodiment, the cell concentrator is provided with an internal shelf in each well extending from the rear chamber surface partially toward the front chamber surface and a bibulous pad disposed below the shelf. A fluid specimen is spaced from the bibulous pad by the shelf when the chamber is tilted prior to centrifugation. After centrifugation, as the concentrator pivots back to the tilted position, carrier fluid flows past the shelf and is absorbed by the bibulous pad. This arrangement eliminates the need for aspiration of carrier fluid following centrifugation without disadvantageously absorbing cells and preventing their attachment to the slide.

The bibulous pad may comprise a single pad of substantially uniform absorbency. Alternatively, the bibulous pad may comprise a first higher absorbency pad portion and a second lower absorbency portion, with the first pad portion disposed below the shelf and the second portion disposed below the pad and extending toward the slide. With this arrangement, the second portion provides a wicking action to slowly absorb carrier fluid from the slide surface during centrifugation and to draw such fluid toward the adjacent, higher absorbency pad portion for absorption and retention. The use of separate materials for the wick and the pad allows the exact selection of material for each disparate purpose.

The rate of wicking is controlled by the composition of the wick and not from poorly controlled attempts at compression of a material not at all ideal for use as a wick.

BRIEF DESCRIPTION OF THE DRAWINGS

The foregoing features of this invention, as well as the invention itself, may be more fully understood from the following detailed description of the invention in which.

DESCRIPTION OF THE PREFERRED EMBODIMENT

Figure 1:
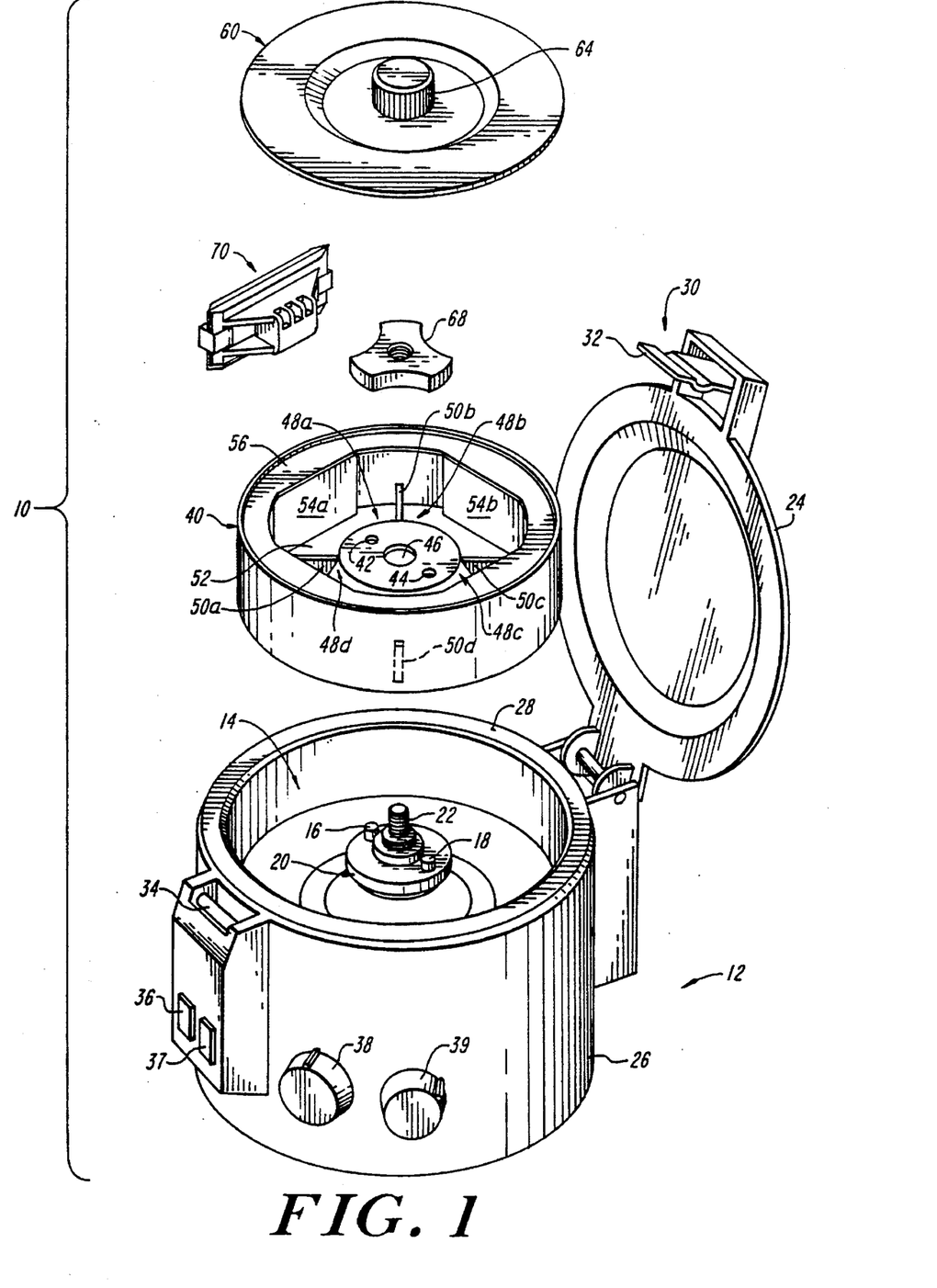
FIG. 1 is an exploded isometric view of centrifuge apparatus in accordance with the present invention.

Referring to FIG. 1, an exploded view of centrifugation apparatus 10 is shown to include an electromechanical spinner 12, a rotor 40, and a cytology cell concentrator 70. The spinner 12 supports the rotor 40 for rotation. Two or four cell concentrators (only an exemplary one 70 of which is shown and described for simplicity) are positioned in the rotor 40 for rotation therewith. The concentrator 70 is adapted to receive a fluid specimen for centrifugation. Exemplary specimens are carrier fluids having cells suspended therein and include normal body fluids such as synovial or cerebrospinal fluid, abnormal fluids such as ascites resulting from a cancer, and artificial fluids such as cell cultures.

The spinner 12 includes a housing 26 having a central depression, or bowl 14 for removably supporting the rotor 40 for rotation. More particularly, a rotor mount 20 is centrally located in the spinner bowl 14 for mounting the rotor 40. The rotor mount 20 has a vertically extending threaded shaft 22 coupled to a motor 19 (shown schematically in FIGS. 6 and 7) for rotation. The rotor 40 includes a pair of indexing holes 42, 44 for engaging complementary indexing pins 16, 18 extending upward from the rotor mount 20. The spinner shaft 22 extends through a central aperture 46 of the rotor 40. The rotor 40 is secured to the spinner 12 with a threaded rotor hold-down nut 68 which engages the threaded shaft 22.

A lid 24 is provided to cover the bowl 14 and the rotor 40 contained therein. A seal for the spinner bowl 14 is provided by a gasket 28 disposed around the perimeter of the bowl 14 and compressed by the lid 24 in closure. A latch mechanism 30 is provided to securely latch the lid 24 in a closed position over the spinner bowl 14 and includes a latch lever 32 coupled to the lid 24 and a latch pin 34 coupled to the spinner housing 26. The latch mechanism 30 is operable for manual latching and unlatching of the lid 24 and also includes an electrically operable automatic lock feature for preventing operation of the centrifuge 10 when the lid 24 is not completely closed and latched and for preventing the lid 24 from being opened during centrifugation.

The spinner 12 has several conventional controls including a start button 36 which initiates a pre-timed centrifugation cycle at a pre-selected speed and a stop button 37 which interrupts the cycle by stopping centrifugation and releasing the latch mechanism 30. Additional controls include a time selector 38 for selecting the duration of centrifugation and a speed selector 39 for selecting the speed of rotation, such as between approximately 1000 and 5000 rpm. The illustrative spinner 12 has a height of approximately five inches, a diameter of approximately seven inches, and a weight of less than approximately four pounds.

The rotor 40 has a plurality of positions 48a–d, each adapted for receiving a cell concentrator, like exemplary concentrator 70. In the illustrative embodiment described herein, the rotor 40 has four positions 48a–d for receiving up to four concentrators. More particularly, the plurality of rotor positions 48a–d are defined by a plurality of ridges, or vertical separating walls 50a–d which separate adjacent positions 48a–d. Each position 48a–d is additionally bordered by a slanted sidewall of a raised central portion 58 of the rotor 40 (FIGS. 6 and 7) and an inner sidewall 54a–d of the rotor 40.

As will be described, the cell concentrators, like exemplary concentrator 70, are shaped to rest stably on a planar surface, such as the bottom surface 52 of the rotor 40, in an advantageous tilted position. Suffice it here to say that each cell concentrator 70 is placed unrestrained in one of the rotor positions 48a–d in the resting, tilted position. When the rotor 40 is rotated, the cell concentrator 70 is forced to pivot to a vertical orientation in which the concentrator 70 contacts the adjacent inner sidewall 54a–d (only two of which 54a, b are shown in the view of FIG. 1). Upon termination of rotation, the concentrator 70 pivots back to the resting, tilted position.

A cover 60 is provided for covering the rotor 40 and rests on a top ledge 56 of the rotor 40 around the perimeter thereof. The cover 60 has a central aperture through which the spinner shaft 22 extends. A threaded nut 64 is provided to engage the threaded spinner shaft 22 and hold the cover 60 in secure position over the rotor 40. The ledge 56 has a layer of compressible material 66 disposed thereover (FIGS. 6 and 7) so that when the cover 60 is in place and the nut 64 is tightened, the compressible layer 66 is somewhat compressed in order to provide an effective seal for the rotor 40.

The ledge 56 and cover 60 prevent the formation of potentially harmful aerosols. More particularly, even if the cell concentrator 70 is overfilled with a fluid specimen, the excess fluid will leave the concentrator 70 as soon as the concentrator begins to pivot to the vertical position and while the rotor 40 is still rotating at a relatively slow speed. Such fluid will flow to the proximal inner sidewall 54a–d of the rotor 40 and be trapped under the top ledge 56. With this arrangement, the formation of potentially harmful aerosols, such as may occur when such fluid is flung at a relatively high speed onto a distant surface, is prevented.

Figure 2:
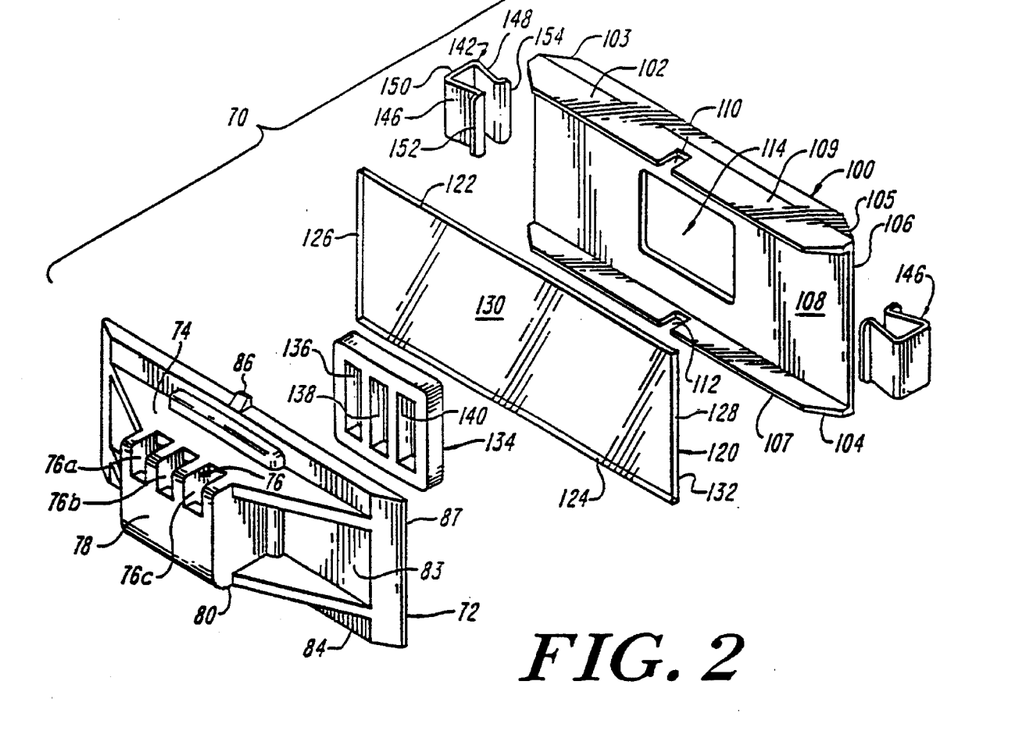
FIG. 2 is an exploded isometric view of the exemplary cytology cell concentrator assembly of FIG. 1.
Figure 2A:
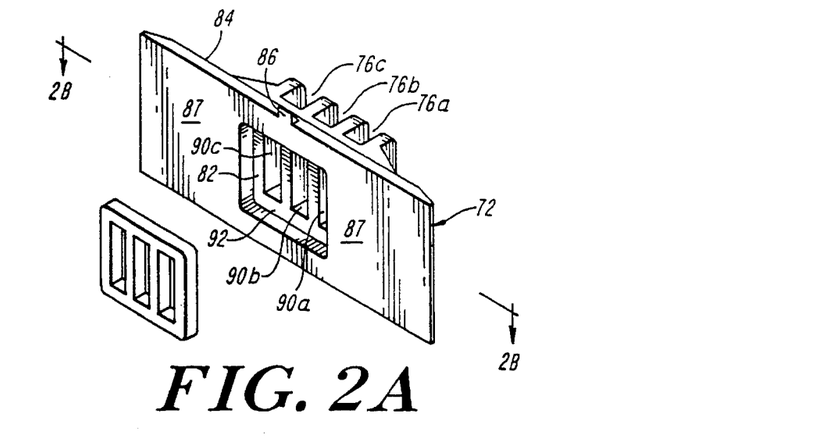
FIG. 2A is an alternate isometric view of the cell concentrator chamber of FIG. 2.
Figures 2B, 3, 4:
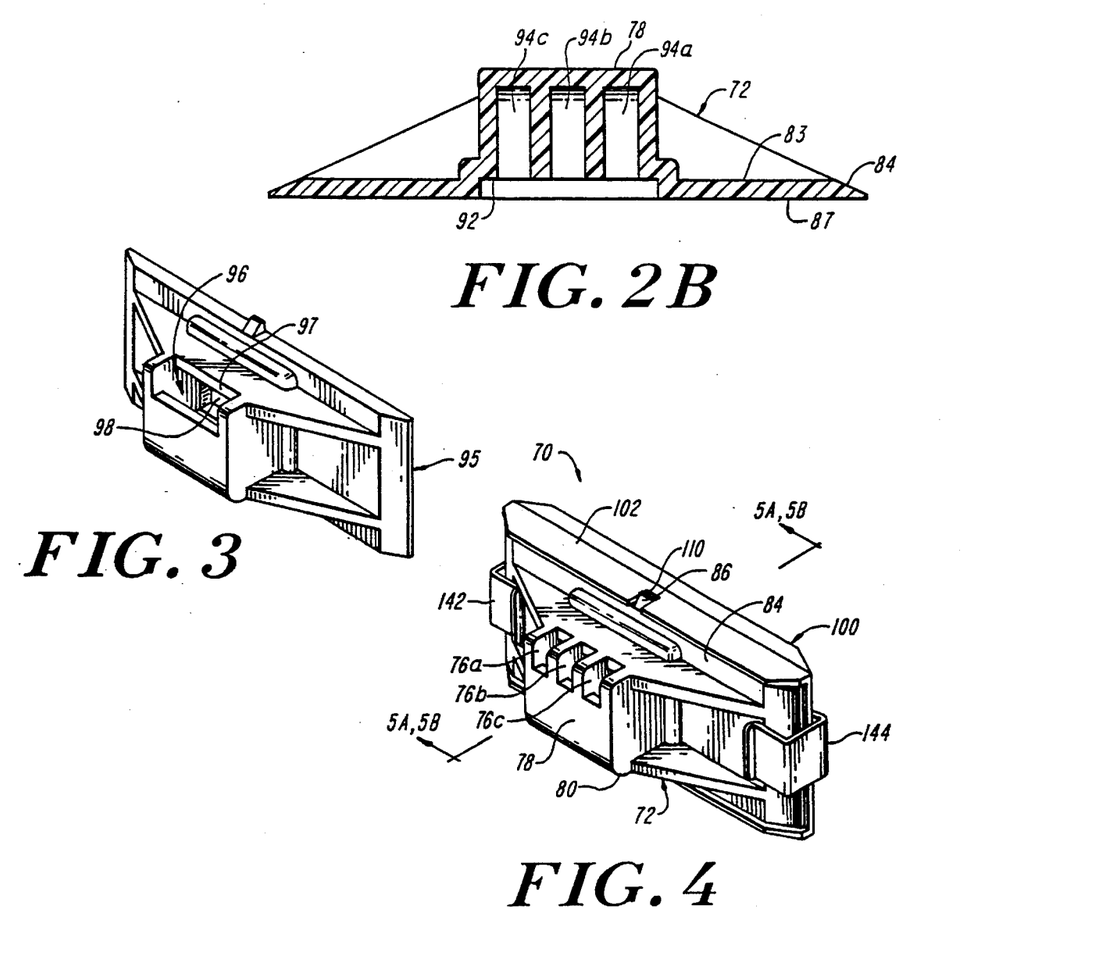
FIG. 2B is a cross-sectional view of the cell concentrator chamber of FIG. 2A.
FIG. 3 is an isometric view of an alternate embodiment of the cell concentrator chamber of FIG. 2.
FIG. 4 is an isometric view of the assembled cell concentrator assembly of FIG. 2.

Referring to FIGS. 2, 2A, and 2B, exemplary cell concentrator 70 is shown to include a chamber 72, a backing plate 100, a seal 134, and clips 142, 144. In assembly, a microscope slide 120 is positioned between the chamber 72 and the backing plate 100 for receiving cells from a fluid specimen during centrifugation. The slide 120 has a top edge 122, a bottom edge 124, side edges 126, 128, a front surface 130, and a rear surface 132, as shown.

The chamber 72 has a mounting flange 84 around the perimeter thereof with a front surface 87 (FIG. 2A) and a rear surface 83. A locator tab 86 protrudes from the top of the mounting flange 84, as shown, for aligning the chamber 72 with the backing plate 100, as will be described. Extending from the mounting flange 84 is a top chamber surface 74 in which one or more fluid receiving apertures 76a–c are disposed, a rear chamber surface 78, and a bottom chamber surface 80. A front chamber surface 82 has one or more fluid expulsion apertures 90a–c disposed therein. Each fluid receiving aperture 76a–c and fluid expulsion aperture 90a–c pair, respectively, defines a well 94a–c of the concentrator 70. The fluid receiving apertures 76a–c additionally extend along a top portion of the rear chamber surface 78 in order to facilitate insertion of a pipette (not shown) therein for loading a fluid specimen into the desired wells 94a–c and for removing fluid therefrom by aspiration.

The fluid expulsion apertures 90a–c are centrally located in the front chamber surface 82 and are slightly depressed in the surface 82 in order to provide a ledge 92 for receiving the seal 134 in assembly. The seal 134 is comprised of an elastomeric material, such as silicone rubber, and, in assembly, provides a fluid seal between the chamber 72 and the slide 120, as will become apparent. To this end, the seal 134 has a plurality of openings 136, 138, and 140, each one corresponding to one of the wells 94a–c of the chamber 72 and being aligned with a corresponding one of the fluid expulsion apertures 90a–c, respectively. The area of the slide 120 adjacent to each seal opening 136–140 is approximately 40 mm$^2$.

Each of the wells 94a–c is adapted to receive a sample volume of approximately 200 microliters. Although the wells 94a–c have an actual volumetric capacity of approximately 450 microliters (referred to as the dead volume), the 200 microliter volume is the fluid amount that can be contained without having the fluid contact the microscope slide 120 when the concentrator 70 is assembled and positioned in its tilted, resting position. The wells 94a–c are relatively shallow, with a height from the top chamber surface 74 to the bottom surface 80 of approximately 1.2 centimeters. Various materials are suitable for fabricating the chamber 72 and backing plate 100, such as plastic. Preferably, the chamber 72 is comprised of a substantially transparent, or clear, plastic to enable viewing of a sample therein. Fiber filled plastic is preferred for use in fabricating the backing plate 100 in order to provide advantageous strength characteristics. The concentrator components (i.e., the chamber 72, backing plate 100, and clips 142, 144) may be re-used after appropriate sterilization or, alternatively, may be discarded after a single use. To this end, the cell concentrator components are preferably comprised of a material capable of being sterilized by steam.

The multiple well concentrator 70 permits simultaneous processing of multiple fluid samples. For example, it may be desirable to process three different concentrations of the same cell suspension fluid in the concentrator 70. This technique allows a user who is uncertain of the cell concentration of a fluid specimen to have adequate cell coverage without requiring a preliminary assessment of cell concentration. Alternatively, it may be desirable to process the same number of cells on the three slide locations adjacent to the three fluid expulsion apertures 90a–c and to treat each of the three cell depositions with a different diagnostic staining process in order to emphasize different cell characteristics or to develop an optimum staining process.

Referring to FIG. 3, a single well chamber embodiment 95 is shown to include analogous surfaces to the multiple well chamber 72 of FIGS. 2, 2A, and 2B but with only a single fluid receiving aperture 97 and fluid expulsion aperture 98. The dead volume of the single well 96 is approximately 1.8 milliliters and thus, its use may be desirable where larger fluid samples are to be analyzed. The single well chamber 95 is used with a fluid seal (not shown) like seal 134 of FIG. 2 but with only a single, central opening for bordering the single fluid expulsion aperture 98 in order to ensure sealed fluid communication between the well 96 and an adjacent microscope slide. The area of a slide bordered by the single well seal is approximately 200 mm².

The backing plate 100 has a protruding top edge 102, a protruding bottom edge 104, a front surface 108, and a rear surface 106, as shown in FIG. 2. Rear portions 103, 105 of the top and bottom backing plate edges 102, 104 are chamfered. Front portions 107, 109 of the top and bottom backing plate edges 102, 104 are beveled to permit the plate 100 to rest stably on a planar surface in a tilted position. The top and bottom backing plate edges 102, 104 provide vertical alignment of the slide 120 and chamber 72 in assembly. Locating notches 110, 112, complementary to the locator tab 86 of the chamber 72, are provided in the top and bottom backing plate edges 102, 104 to permit dual orientation mating of the chamber 72 with backing plate 100. The notch and tab arrangement prevents the chamber 72 from sliding relative to the backing plate 100 in disassembly. Since either the top or bottom edge 102, 104 may be the "operational bottom edge" (i.e., placed on the bottom rotor surface 52), both such surfaces 102, 104 have front beveled portions 107, 109 to ensure the tilted concentrator orientation regardless of the orientation of the backing plate 100. Also provided is a viewing aperture 114 in the backing plate 100 which permits viewing of cells deposited on the slide 120 during processing, as will be discussed.

A securing mechanism, including clips 142, 144, is provided for securing, or clamping the backing plate 100 to the chamber 72, with the slide 120 sandwiched therebetween. Each of the clips 142, 144 has a pair of opposing, resilient arms 146, 148 (as labelled on exemplary clip 142) spaced by an edge 150. Flared end portions 152, 154 of each of the resilient arms 146, 148 are provided for facilitating removal of the clips during disassembly of the concentrator 70. It is noted that while the chamber 72, the backing plate 100, and the securing clips 142, 144 are shown to be separate components, one or more of these components may be integrally fabricated.

Referring also to FIG. 4, in assembly of the concentrator 70, the slide 120 is positioned on the backing plate 100 so that the rear surface 132 of the slide 120 is adjacent to the front backing plate surface 108 with the protruding top and bottom backing plate edges 102, 104, covering the top and bottom slide edges 122, 124, respectively. The chamber 72, with the seal 134 disposed on the ledge 92, is positioned over the backing plate 100 and slide 120 with the chamber tab 86 located in one of the backing plate notches 110, 112. Thereafter, slight pressure is applied to hold the chamber 72 and the backing plate 100 together as the clips 142, 144 are pushed over the ends of the concentrator assembly 70. Specifically, in assembly, a first one 146 of the resilient arms 146, 148 of each clip 142, 144 contacts an edge portion of the rear surface 83 of the mounting flange 84 and a second one 148 of the resilient arms 146, 148 contacts the rear backing plate surface 106.

Figure 5A:
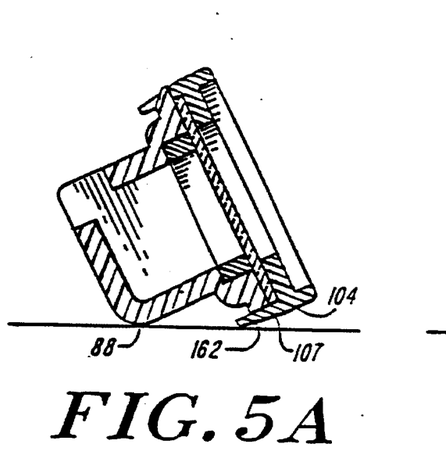
FIG. 5A is a cross-sectional view of the assembled cell concentrator assembly of FIG. 4.
Figure 5B:
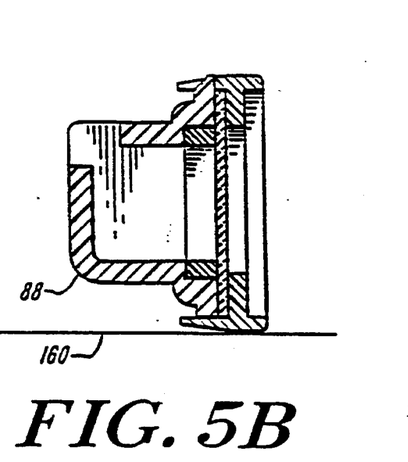
FIG. 5B is an alternate cross-sectional view of the assembled cell concentrator assembly of FIG. 4.

Referring to FIGS. 5A and 5B, cross-sectional views of the assembled concentrator 70 of FIG. 4 are shown. Specifically, FIG. 5A shows the concentrator 70 positioned in a tilted, resting position over a planar surface 160 due to the beveled front portion 107 of the backing plate edge 104. The concentrator 70 rests stably in this position with an edge 88 of the chamber 72 between the rear chamber surface 78 and the bottom chamber surface 80 (FIG. 2) and a front portion 162 of the bottom backing plate edge 104 in contact with the surface 160.

With this arrangement, the concentrator 70 is stable in the tilted position of FIG. 5A when positioned on a planar surface (i.e., such as a laboratory table or the bottom surface 52 of the rotor 40) for transfer of a fluid specimen into the wells 94a–c. The tilt of the concentrator 70 causes the fluid to be kept away from the front chamber surface 82 by gravity, thereby also keeping such fluid away from the slide 120. Preventing the fluid from contacting the slide 120 prior to centrifugation improves the uniformity of the resulting cell deposition.

During centrifugation, the concentrator 70 is centrifugally forced to pivot to the vertical position shown in FIG. 5B. In this position, centrifugal forces on the fluid causes the fluid to be expelled through the fluid expulsion apertures 90a–c onto the slide 120 for deposition of the cells suspended therein.

Figure 6:
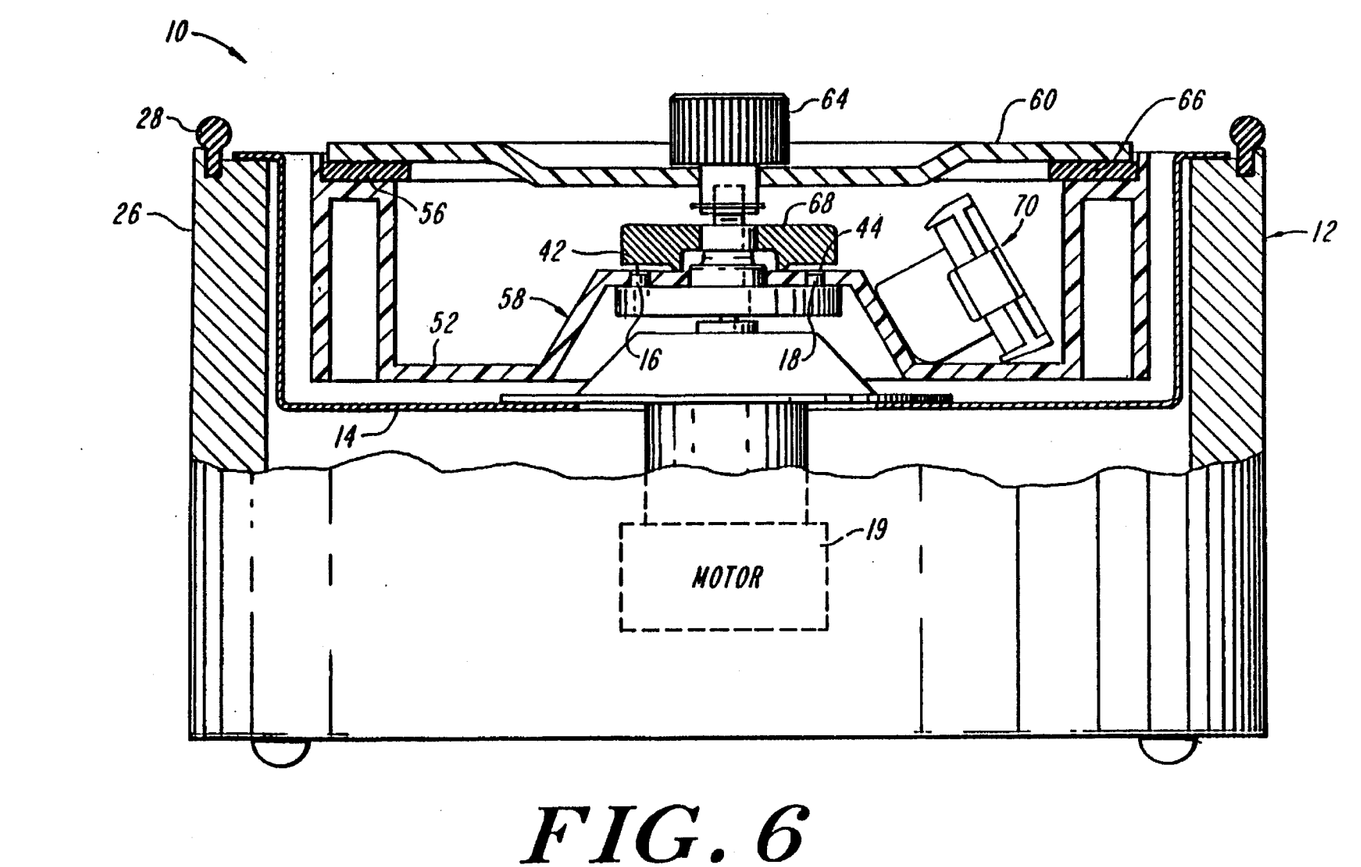
FIG. 6 is a cross-sectional view of the cytology centrifuge apparatus of FIG. 1 prior to centrifugation.

Referring to FIG. 6, a cross-sectional view of the spinner 12 is shown with the rotor 14 positioned therein. Although only exemplary concentrator 70 is shown in the rotor 40 in FIGS. 6 and 7, it is desirable to balance the rotor 40 by rotating an even number of concentrators, with concentrators having like chambers positioned opposite each other. Generally, the concentrators are placed in the rotor 40 after having specimen fluids inserted therein. In certain applications where there may be a biohazard, it may be desirable to transfer the specimens to the concentrators 70 in a safety cabinet. In fact, the entire spinner 12 may be moved to such a safety environment for loading specimens into the concentrators and placement of the concentrators in the rotor 40 due to the low weight and small size of the spinner unit 12.

As previously mentioned, the concentrators are placed in the rotor 40 in their resting, tilted position. The separating walls 50a–d of the rotor and the slanted sidewalls of the central raised portion 58 of the rotor prevent inadvertent tipping over of the concentrators, such as may occur when medical personnel load sample fluids into the concentrators or aspirate fluids therefrom. In this position, a sample fluid may be transferred into each of the desired wells 94a–c by inserting a pipette containing the sample through the fluid receiving apertures 76a–c, respectively. The tilting of the concentrators advantageously keeps the fluid away from the adjacent slide.

Figure 7:
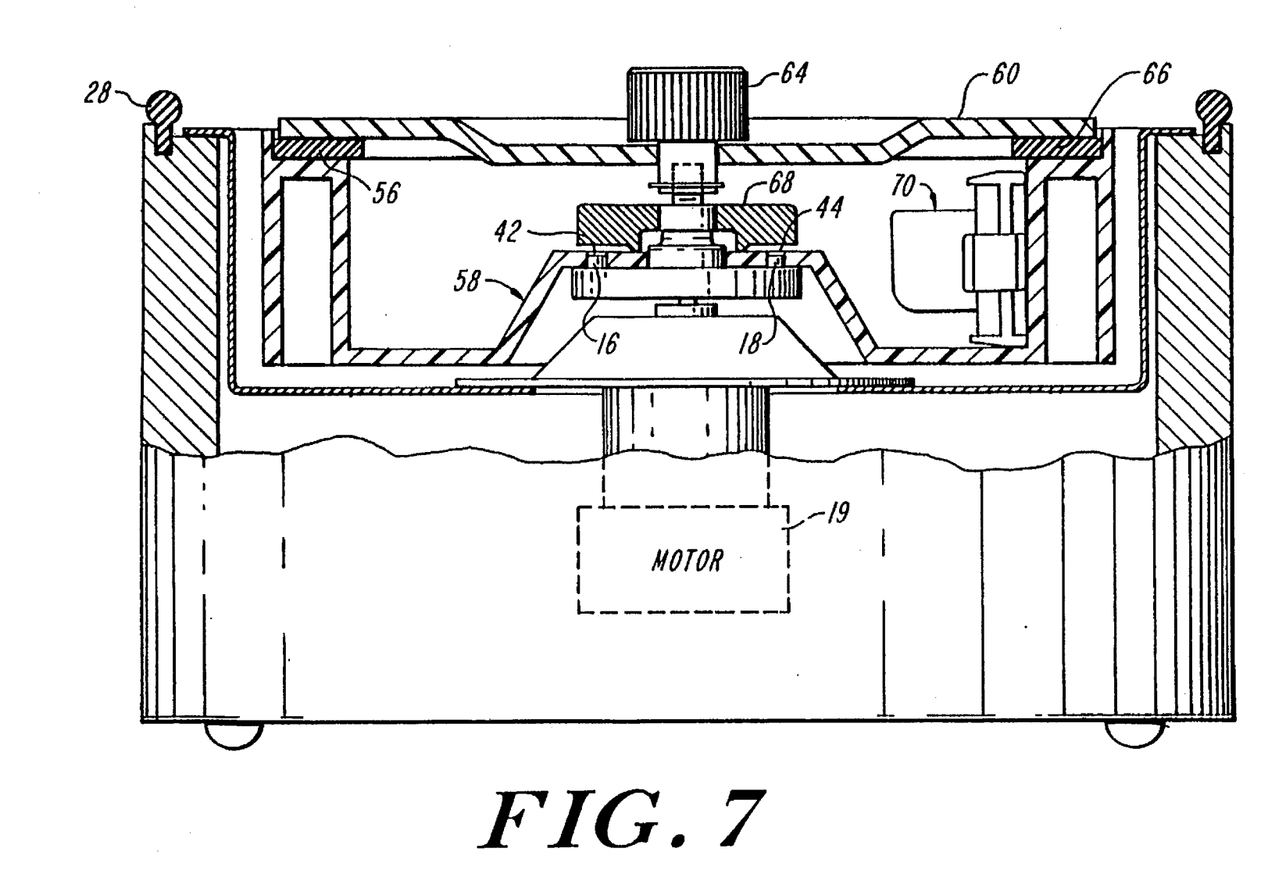
FIG. 7 is a cross-sectional view of the cytology centrifuge apparatus of FIG. 1 during centrifugation.

Referring to FIG. 7, when the spinner 12 is activated and the shaft 22 is rotated by the motor 19, concomitant rotation is imparted to the rotor 40 and the concentrators contained therein. The centrifugal force causes the concentrator 70 to pivot to the vertical orientation shown so that the backing plate 100 contacts the corresponding rotor inner sidewall 54a–d. In this position, the fluid contained in the wells 94a–c is expelled through the fluid expulsion apertures 90a–c, respectively, and onto the slide 120 to which suspended cells attach.

Once rotation of the rotor 40 is terminated, the cell concentrator 70 returns to the tilted position (shown in FIG. 6). That is, the cessation of rotation causes the concentrator 70 to automatically pivot back to the tilted position because of the beveled front portion 107 of the backing plate edge 104. Carrier fluid may be removed by aspiration with a pipette inserted through the fluid receiving apertures 76a–c. Both the insertion of specimen fluids into the wells 94a–c and aspiration of carrier fluid therefrom is facilitated by the preferred clear plastic construction of the chamber 72 which permits viewing of the fluid loading and unloading process. Other features of the concentrator 70 which facilitate loading and/or unloading fluid specimens include the shallowness of the wells 94a–c and the automatic return of the concentrator to the tilted position after centrifugation. That is, since the concentrator is tilted after centrifugation, with the carrier fluid kept away from the slide 120, a pipette inserted to remove the carrier fluid will not interfere with the deposited cells.

Once carrier fluid is removed, the deposited or sedimented cells may be stained in the still assembled concentrator 70 by any of various fixing and staining procedures. Or, when the cell concentration of the sample fluid is very low, additional aliquots of the specimen can be added and reprocessed, or respun, to increase the number of cells on the slide 130. When the concentrator 70 is used as a staining chamber, staining reagents may be inserted into the wells 94a–c through the fluid receiving apertures 76a–c and brought into contact with the deposited cells by inverting the concentrator 70 so that so that the slide is resting in a horizontal orientation. With the concentrator 70 in this position, the reagents flow through the corresponding fluid expulsion apertures 90a–c, respectively, to contact and flow onto the slide 120. The concentrator 70 is effective as a staining chamber since there is no bibulous paper disposed between the chamber and the slide which would absorb the expensive staining reagents. Features of the concentrator 70 which enhance its use as a staining chamber include the shallowness and small volume capacity of the wells 94a–c which prevent waste of expensive staining reagents. Moreover, use of the concentrator for staining minimizes reagent waste due to evaporation since the wells 94a–c are substantially closed.

The deposited cells may be analyzed under a microscope during the staining process without disassembling the concentrator 70 through the viewing aperture 114 of the backing plate 100. More particularly, the concentrator 70 may be inverted with the rear well surface 78 placed on a microscope stage in order to view the sedimented and attached cells through the viewing aperture 114 and from the rear surface 132 of the slide 120. Alternatively, an inverted microscope may be utilized in which the objective lens is below the stage, thereby eliminating the need to invert the concentrator 70. Thus, with an inverted microscope, the concentrator 70 can be placed on the stage with the backing plate 100 down. Viewing the deposited cells during the staining process is advantageous in the development and perfection of optimum staining processes. Note that alternatively, the backing plate 100 may be comprised of a transparent material and the cells viewed through the transparent backing plate, without providing a window therein.

Figure 8A:
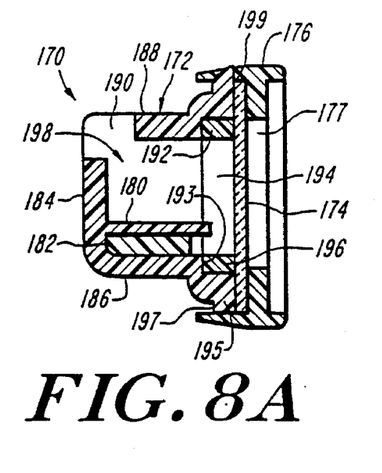
FIGS. 8A–8D are cross-sectional views of an alternate embodiment of the cell concentrator assembly of FIG. 2 at various stages of centrifugation.

Referring to FIG. 8A, an alternate embodiment 170 of the concentrator 70 is shown to include like components assembled in the manner described above in conjunction with concentrator 70. More particularly, the concentrator 170 includes a chamber 172 having at least one well 198, a slide 174, a backing plate 176 with a viewing aperture 177, and clips (not shown) for securing the chamber 172 to the backing plate 176. The chamber 172 has surfaces analogous to those of chamber 72 (FIG. 2) providing the same advantages described above in conjunction with the resting, tilted position of the concentrator 70. More particularly, the chamber 172 has a mounting flange 195 having a front surface 199 and a rear surface 197. Extending from the mounting flange 195 is a bottom chamber surface 186, a top chamber surface 188 in which at least one fluid receiving aperture 190 is disposed, and a rear chamber surface 184. A front chamber surface 193 has at least one fluid expulsion aperture 194 disposed therein in a depressed manner to provide a ledge 192 for receiving a fluid seal 196, like the seal 134 described above.

The concentrator 170 additionally includes an internal shelf 180 extending from the rear chamber surface 184 partially toward the front chamber surface 193 and the front surface of the slide 174, as shown. Also provided is a layer of bibulous paper, or a bibulous pad 182, disposed below the shelf 180 on the bottom of the chamber 172. The bibulous pad 182 is provided to absorb carrier fluid so that aspiration of fluid after centrifugation can be avoided.

Figure 8B:
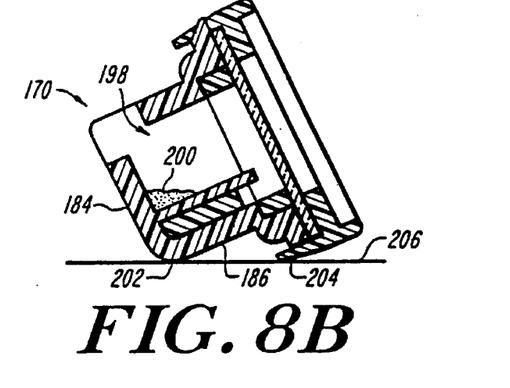

Referring to FIG. 8B, the concentrator 170 is shown in its resting, tilted position in which an edge 202 of the chamber 170 between the rear surface 184 and the bottom surface 186 and a front portion 204 of the bottom backing plate edge 176 contact the planar surface 206, in the manner described above in conjunction with FIG. 5B. A fluid sample 200 is disposed in the well 198 and, due to the tilted position of the concentrator 170, is kept away from the front chamber surface 193, as discussed above.

Figure 8C:
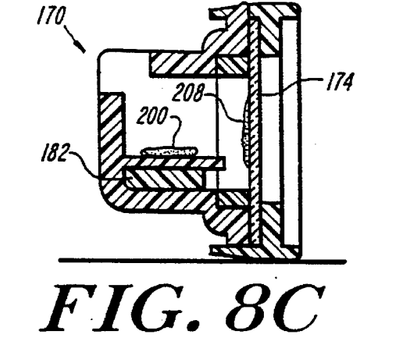
Figure 8D:
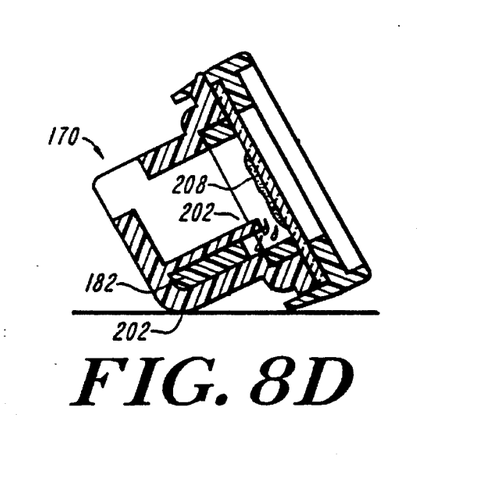

During centrifugation, the concentrator 170 pivots to the vertical position shown in FIG. 8C and cells 208 suspended in the fluid 200 are deposited on the slide 174 as the carrier fluid 200 is propelled toward and held against the slide. After rotation has terminated, the concentrator 170 returns to its resting, tilted position, as shown in FIG. 8D. As the concentrator 170 pivots back toward the tilting position, carrier fluid 200 flows down the slide 174 and towards the chamber edge 202, as shown. As the carrier fluid flows under the shelf 180, it contacts and is absorbed by the bibulous pad 182. With the shelf 180 and bibulous pad 182 described above, aspiration of carrier fluid is avoided. Moreover, the potential drawbacks typically associated with the use of bibulous paper are eliminated. More particularly, since the bibulous pad 182 is not disposed between the chamber 172 and the slide 174 as in conventional arrangements, compression of the pad is not required to control the rate and capacity of fluid absorption. Additionally, since the bibulous pad 182 is not in, or adjacent to the path of the fluid as it is forced against the slide, potential problems including premature carrier fluid absorption, loss of cells to the bibulous pad, and contamination of the deposited cells by filaments of the bibulous pad are avoided.

Figure 9:
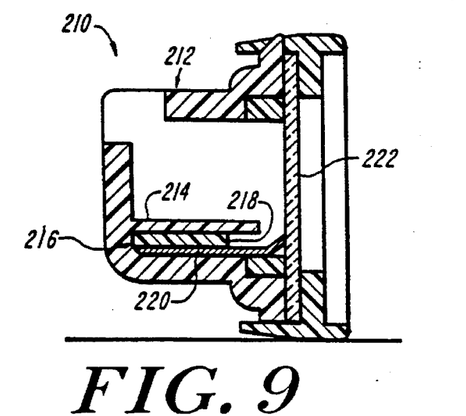
FIG. 9 is a cross-sectional view of a further alternate embodiment of the cell concentrator assembly of FIG. 2.

Referring to FIG. 9, a further alternate embodiment 210 of the cell concentrator is shown to include like components and surfaces to concentrator 170 of FIGS. 8A–D. More particularly, the chamber 212 of the concentrator 210 includes an internal shelf 214 like shelf 180 described above. Disposed under shelf 214 is a bibulous pad 216 comprised of a first bibulous pad portion 218 having a first relatively high fluid absorbing capacity and a second portion 220 having a second lower fluid absorbing capacity, preferably significantly lower than the first fluid absorbing capacity to serve as a wick.

More particularly, the higher absorbency pad portion 218 is disposed under the shelf 214. The second, lower absorbency portion 220 extends from the first portion 218 toward the slide 222 and may contact the slide 222, as shown. With this arrangement, the lower absorbency portion 220 provides wicking of carrier fluid causing such fluid to be absorbed relatively slowly and transferred to the bibulous pad. The higher absorbency pad portion 218 on the other hand quickly absorbs a larger amount of fluid than the second portion 220.

The concentrator 210 is disposed in the same positions as shown in FIGS. 8B–D prior to centrifugation, during centrifugation, and after centrifugation, respectively. Thus, although the lower absorbency portion 220 is in contact with the slide 222, absorption of carrier fluid thereby is prevented prior to centrifugation by the tilted position of the concentrator 210, as shown in FIG. 8B for concentrator 170. As soon as the rotor is rotated and the carrier fluid is forced toward and held against the slide 222, the lower absorbency portion 220 begins to draw fluid from the slide 222 toward the higher absorbency pad portion 218. Because of the relatively slow rate of absorption of the wicking portion 220 and its position at the bottom of the slide area in fluid communication with the chamber 212, premature absorption of carrier fluid and cells is avoided. Moreover, like the bibulous pad 182 of the embodiment of FIGS. 8A–D, compression of the pad in order to control the rate and capacity of fluid absorption is unnecessary since the wicking rate is controlled by the composition of the wick portion 220. Thus, this arrangement, like that of FIGS. 8A–D, eliminates the need for the user to evacuate carrier fluid from the chamber prior to further processing without disadvantageously absorbing significant fluid prior to successful deposition of the cells.

Having described the preferred embodiments of the invention, it will be apparent to one of skill in the art that other embodiments incorporating their concepts may be used. Accordingly, the invention should be limited only by the spirit and scope of the appended claims.

We claim:

1. Centrifuge apparatus comprising:

a spinner having a central depression;

a rotor removably supported for rotation in said central depression of said spinner, said rotor having a substantially planar bottom surface portion; and a cell concentrator disposed in said rotor for receiving a fluid specimen for centrifugation, said cell concentrator comprising:
   a chamber having a top surface in which a fluid receiving aperture is disposed, a bottom surface, a front surface bordered by a mounting flange and having a fluid expulsion aperture disposed therein, and a rear surface;
   a backing plate having a top edge, a bottom edge, a front surface adjacent to said front chamber surface, and a rear surface; and
   a securing mechanism for securing said backing plate to said chamber, wherein said cell concentrator is stable when rested on said substantially planar bottom surface portion of said rotor prior to rotation of said rotor, with a front edge of said bottom chamber surface and said bottom backing plate edge contacting said substantially planar bottom surface portion of said rotor so that received fluid specimen is kept away from said front chamber surface and toward said substantially planar bottom surface portion of said rotor.

2. The apparatus recited in claim 1 wherein said apparatus further includes a slide disposed between said backing plate and said chamber so that said fluid expulsion aperture of said chamber is in fluid communication with a central portion of said slide and said mounting flange is adjacent to a perimeter portion of said slide.

3. The apparatus recited in claim 2 wherein said chamber includes three wells, each having a corresponding fluid receiving aperture disposed in said top chamber surface and a corresponding fluid expulsion aperture disposed in said front chamber surface.

4. The apparatus recited in claim 2 wherein said chamber is comprised of a substantially transparent plastic.

5. The apparatus recited in claim 2 wherein said cell concentrator further comprises a fluid seal bordering said fluid expulsion aperture and said central portion of said slide to provide a fluid seal between said fluid expulsion aperture and said central portion of said slide.

6. The apparatus recited in claim 2 wherein said securing mechanism comprises a pair of clips, each one having opposing resilient surfaces spaced by an edge, wherein a first one of said opposing resilient surfaces contacts said mounting flange of said chamber and a second one of said opposing resilient surfaces contacts said rear backing plate surface.

7. Centrifuge apparatus comprising:

a spinner having a central depression;

a rotor removably supported for rotation in said central depression of said spinner;

a cell concentrator disposed in said rotor for receiving a fluid specimen for centrifugation, said cell concentrator comprising:
   a chamber having a top surface in which a fluid receiving aperture is disposed, a bottom surface, a front surface bordered by a mounting flange and having a fluid expulsion aperture disposed therein, and a rear surface;
   a backing plate having a top edge, a bottom edge, a front surface adjacent to said front chamber surface, and a rear surface; and
   a securing mechanism securing said backing plate to said chamber, wherein said cell concentrator is stable when rested on a planar surface with a front edge of said bottom chamber surface and said bottom backing plate edge contacting said planar surface so that said received fluid specimen is kept away from said front chamber surface and toward said planar surface; and
   a slide disposed between said backing plate and said chamber so that said fluid expulsion aperture of said chamber is in fluid communication with a central portion of said slide and said mounting flange is adjacent to a perimeter portion of said slide, wherein said backing plate has a viewing aperture in alignment with said fluid expulsion aperture of said chamber to enable viewing of cells on said slide.

8. A cell concentrator comprising:

a chamber having a top surface in which a fluid receiving aperture is disposed, a bottom surface having an elongated front edge, a front surface bordered by a mounting flange and having a fluid expulsion aperture disposed therein, and a rear surface;

a backing plate having a top edge, a bottom edge substantially parallel to said elongated front edge of said bottom chamber surface, a front surface adjacent to said front surface of said chamber, and a rear surface; and a securing mechanism securing said backing plate to said chamber, wherein said concentrator is stable when rested on a planar surface with said elongated front edge of said bottom chamber surface and said bottom backing plate edge contacting said planar surface so that received fluid specimen is kept away from said front chamber surface and toward said planar surface.

9. The cell concentrator recited in claim 8 further including a slide disposed between said front backing plate surface and said front chamber surface so that said fluid expulsion aperture of said chamber is in fluid communication with a central portion of said slide and said flange of said chamber is adjacent to a perimeter portion of said slide.

10. The cell concentrator recited in claim 9 further comprising a fluid seal bordering said fluid expulsion aperture and said central portion of said slide to provide a fluid seal between said fluid expulsion aperture and said central portion of said slide.

11. The cell concentrator recited in claim 8 wherein said chamber includes three wells defined by said top, bottom, and front surfaces, said fluid receiving aperture being defined by an aperture disposed in said top chamber surface of each of said wells and a fluid expulsion aperture being defined by an aperture disposed in said front chamber surface of each of said wells.

12. A cell concentrator comprising:

a chamber having a top surface in which a fluid receiving aperture is disposed, a bottom surface, a front surface bordered by a mounting flange and having a fluid expulsion aperture disposed therein, and a rear surface;

a backing plate having a top edge, a bottom edge, a front surface adjacent to said front surface of said chamber, and a rear surface; and a securing mechanism for securing said backing plate to said chamber, wherein said concentrator is stable when rested on a planar surface with a front edge of said bottom chamber surface and said bottom backing plate edge contacting said planar surface so that received fluid specimen is kept away from said front chamber surface and toward said planar surface, wherein said backing plate has a viewing aperture in alignment with said fluid expulsion aperture of said chamber to enable viewing of cells on said slide.

13. A cell concentrator comprising:

a chamber having a top surface in which a fluid receiving aperture is disposed, a bottom surface, a front surface bordered by a mounting flange and having a fluid expulsion aperture disposed therein, and a rear surface;

a backing plate having a top edge, a bottom edge, a front surface adjacent to said front chamber surface, and a rear surface having a viewing aperture therein aligned with said fluid expulsion aperture of said chamber to enable viewing of cells on a slide disposed between said chamber and said backing plate; and a securing mechanism for securing said backing plate to said chamber.

14. The cell concentrator recited in claim 13 further comprising a fluid seal bordering said fluid expulsion aperture to provide a fluid seal between said fluid expulsion aperture and the slide.

15. The cell concentrator recited in claim 13 wherein said concentrator is stable when rested on a planar surface with a front edge of said bottom chamber surface and said bottom backing plate edge contacting said planar surface so that said received carrier fluid is kept away from said front chamber surface toward said planar surface.

16. The cell concentrator recited in claim 13 wherein said securing mechanism comprises a pair of clips, each one having a opposing resilient surfaces spaced by an edge, wherein a first one of said opposing resilient surfaces contacts said mounting flange of said chamber and a second one of said opposing resilient surfaces contacts said rear backing plate surface.

17. Centrifuge apparatus comprising:

a spinner;

a rotor removably supported for rotation by said spinner, said rotor having a plurality of positions defined by separating walls, each of said plurality of positions having a substantially planar bottom portion; and a cell concentrator disposed unrestrained on said substantially planar bottom portion of one of said plurality of positions of said rotor prior to rotation of said rotor, said cell concentrator comprising:
a chamber having a fluid receiving aperture for receiving a fluid specimen and a fluid expulsion aperture;
a slide in fluid communication with said fluid expulsion aperture of said chamber;
a backing plate for receiving said slide; and
a securing mechanism securing said backing plate to said chamber.

18. The centrifuge apparatus recited in claim 17 wherein said chamber has a top surface in which said fluid receiving aperture is disposed, a bottom surface, a front surface bordered by a mounting flange and having said fluid expulsion aperture disposed therein, and a rear surface and wherein said backing plate has a top edge, a bottom edge, a front surface adjacent to said front chamber surface and a rear surface, wherein said cell concentrator is stable when rested on said substantially planar bottom portion of said rotor position with a front edge of said bottom chamber surface and said bottom backing plate edge contacting said substantially planar bottom portion of said rotor position so that received fluid is kept away from said front chamber surface and toward said substantially planar bottom portion of said rotor position.

19. The centrifuge apparatus recited in claim 17 wherein said securing mechanism comprises a pair of clips, each one having a opposing resilient surfaces spaced by an edge, wherein a first one of said opposing resilient surfaces contacts said mounting flange of said chamber and a second one of said opposing resilient surfaces contacts said rear backing plate surface.

20. The centrifuge apparatus recited in claim 17 wherein said apparatus further comprises a fluid seal bordering said fluid expulsion aperture of said chamber to provide a fluid seal between the fluid expulsion aperture and a central portion of said slide.

21. Centrifuge apparatus comprising:

a spinner;

a rotor removably supported for rotation by said spinner; and a cell concentrator disposed unrestrained in said rotor for receiving a fluid specimen for centrifugation, said cell concentrator comprising:
a chamber having a fluid receiving aperture for receiving said fluid specimen and a fluid expulsion aperture;

a slide in fluid communication with said fluid expulsion aperture of said chamber;

a backing plate for receiving said slide; and a securing mechanism for securing said backing plate to said chamber, wherein said backing plate has a viewing aperture in alignment with said fluid expulsion aperture of said chamber to enable viewing of cells on said slide.

22. Centrifuge apparatus comprising:

a spinner having a central depression and a lid;

a rotor removably supported for rotation in said central depression of said spinner; and at least one cell concentrator disposed in said rotor, said at least one cell concentrator comprising:

a chamber having a top surface, a bottom surface, a front surface bordered by a mounting flange, and a rear surface, said chamber having three wells, each one being associated with a corresponding fluid receiving aperture disposed in said top chamber surface and a corresponding fluid expulsion aperture disposed in said front chamber surface;

a bibulous pad disposed within said chamber;

a slide having a front surface disposed adjacent to said front chamber surface so that said mounting flange is adjacent to a perimeter portion of said slide and said fluid expulsion apertures are adjacent to a central portion of said slide;

a fluid seal disposed adjacent to said front chamber surface around said fluid expulsion apertures to provide a fluid seal between each of said wells and said central portion of said slide;

a backing plate having a front surface disposed adjacent to a rear surface of said slide and having top and bottom protruding edges for vertically aligning said slide and said chamber with said backing plate; and a securing mechanism securing said backing plate to said chamber so that said slide is sandwiched between said backing plate and said chamber.

23. The centrifuge apparatus recited in claim 22 wherein said securing mechanism is a pair of clips, each one having opposing resilient surfaces spaced by an edge, wherein a first one of said opposing resilient surfaces contacts said chamber mounting flange and a second one of said opposing resilient surfaces contacts said rear backing plate surface.

24. The centrifuge apparatus recited in claim 22 wherein said backing plate has a notch and said chamber has a locator tab complementary to said notch so that, when said tab is positioned in said notch, said chamber and said backing plate are horizontally aligned.

25. The centrifuge apparatus recited in claim 22 wherein said rotor has four positions for receiving up to four cell concentrators and wherein said received cell concentrators are disposed unrestrained within a respective position of said rotor.

26. The centrifuge apparatus recited in claim 25 wherein said at least one cell concentrator is stable when rested in one of said positions of said rotor with a front edge of said bottom chamber surface and said bottom backing plate edge contacting a bottom surface of said rotor so that a received fluid is kept away from said front chamber surface and toward said bottom rotor surface.

27. A cell concentrator comprising:

a chamber having a top surface in which a fluid receiving aperture is disposed for receiving a cell carrier fluid for centrifugation, a bottom surface, a front surface in which a fluid expulsion aperture is disposed to permit expulsion of cells from said carrier fluid onto an adjacent slide, and a rear surface, said chamber having a shelf extending horizontally from said rear surface partially toward said front surface, wherein said chamber is tilted prior to centrifugation so that said fluid is kept away from said front chamber surface and said chamber is substantially vertically oriented during centrifugation when said cells are expelled through said fluid expulsion aperture toward said slide;

a bibulous pad disposed within said chamber and below said shelf so that said carrier fluid is spaced from said bibulous pad by said shelf when said chamber is tilted prior to centrifugation and so that carrier fluid flows under said shelf after centrifugation to be absorbed by said bibulous pad;

a backing plate having a front surface adjacent to said slide and a rear surface; and a securing mechanism for securing said backing plate to said chamber with said slide sandwiched therebetween.

28. A cell concentrator comprising:

a chamber having a top surface in which a fluid receiving aperture is disposed for receiving a cell carrier fluid for centrifugation, a bottom surface, a front surface in which a fluid expulsion aperture is disposed to permit expulsion of cells from said carrier fluid onto an adjacent slide, and a rear surface, said chamber having a shelf extending horizontally from said rear surface partially toward said front surface, wherein said chamber is tilted prior to centrifugation so that said fluid is kept away from said front chamber surface and said chamber is substantially vertically oriented during centrifugation when said cells are expelled through said fluid expulsion aperture toward said slide;

a bibulous pad disposed below said shelf so that said carrier fluid is spaced from said bibulous pad by said shelf when said chamber is tilted prior to centrifugation and so that carrier fluid flows under said shelf after centrifugation to be absorbed by said bibulous pad;

a backing plate having a front surface adjacent to said slide and a rear surface; and a securing mechanism for securing said backing plate to said chamber with said slide sandwiched therebetween, wherein said backing plate has a viewing aperture aligned with said fluid expulsion aperture of said chamber to permit viewing of cells attached to said slide.

29. A cell concentrator comprising:

a chamber having a top surface in which a fluid receiving aperture is disposed for receiving a cell carrier fluid for centrifugation, a bottom surface, a front surface in which a fluid expulsion aperture is disposed to permit expulsion of cells from said carrier fluid onto an adjacent slide, and a rear surface, said chamber having a shelf extending horizontally from said rear surface partially toward said front surface, wherein said chamber is tilted prior to centrifugation so that said fluid is kept away from said front chamber surface and said chamber is substantially vertically oriented during centrifugation when said cells are expelled through said fluid expulsion aperture toward said slide;

a bibulous pad disposed below said shelf so that said carrier fluid is spaced from said bibulous pad by said shelf when said chamber is tilted prior to centrifugation and so that carrier fluid flows under said shelf after centrifugation to be absorbed by said bibulous pad;

a backing plate having a front surface adjacent to said slide and a rear surface; and a securing mechanism for securing said backing plate to said chamber with said slide sandwiched therebetween, wherein said bibulous pad comprises a first pad portion having a first fluid absorbing capacity and a second portion having a second fluid absorbing capacity lower than said first fluid absorbing capacity, wherein said first pad portion is disposed under said shelf and said second portion is disposed in fluid communication with said first pad portion and extends from said first pad portion toward said front chamber surface.

* * * * *